United States Patent
Gilbert et al.

(10) Patent No.: US 9,839,469 B2
(45) Date of Patent: *Dec. 12, 2017

(54) SYSTEMS AND METHODS FOR IMPROVING EFFICIENCY OF ELECTROSURGICAL GENERATORS

(71) Applicant: COVIDIEN LP, Mansfield, MA (US)

(72) Inventors: James A. Gilbert, Boulder, CO (US); Mark A. Johnston, Boulder, CO (US); Aaron Mattmiller, Longmont, CO (US); Joshua H. Johnson, Arvada, CO (US)

(73) Assignee: COVIDIEN LP, Mansfield, MA (US)

( * ) Notice: Subject to any disclaimer, the term of this patent is extended or adjusted under 35 U.S.C. 154(b) by 256 days.

This patent is subject to a terminal disclaimer.

(21) Appl. No.: 14/320,804

(22) Filed: Jul. 1, 2014

(65) Prior Publication Data
US 2015/0088118 A1    Mar. 26, 2015

Related U.S. Application Data (60) Provisional application No. 61/881,575, filed on Sep. 24, 2013, provisional application No. 61/881,547, filed on Sep. 24, 2013.

(51) Int. Cl.
*A61B 18/12* (2006.01)
*A61B 18/00* (2006.01)
*A61B 18/14* (2006.01)

(52) U.S. Cl.
CPC .......... *A61B 18/1206* (2013.01); *A61B 18/14* (2013.01); *A61B 2018/00577* (2013.01);
(Continued)

(58) Field of Classification Search
CPC ................ A61B 18/1206; A61B 18/14; A61B 2018/00577; A61B 2018/00601;
(Continued)

(56) References Cited

U.S. PATENT DOCUMENTS 4,473,075 A * 9/1984 Rexroth ................. A61B 18/12
606/37
4,569,345 A * 2/1986 Manes ................... A61B 18/12
331/183
(Continued)

FOREIGN PATENT DOCUMENTS

DE        179607 C      3/1905
DE        390937 C      3/1924
(Continued)

OTHER PUBLICATIONS

Extended European Search Report for EP 14 18 4738 dated Apr. 10, 2015.
(Continued)

*Primary Examiner* — Daniel Fowler (57) ABSTRACT

An electrosurgical generator is presented including a radio frequency (RF) amplifier coupled to an electrical energy source and configured to generate electrosurgical energy, the RF amplifier including an inverter configured to convert a direct current (DC) to an alternating current (AC), and a plurality of sensors configured to sense voltage and current of the generated electrosurgical energy. The electrosurgical generator further includes a controller coupled to the RF amplifier and the plurality of sensors. The electrosurgical may be further configured to determine a power level based on the sensed voltage and the sensed current, determine an efficiency of the electrosurgical generator, and insert a predetermined integer number of off cycles when the efficiency of the electrosurgical generator reaches a threshold power efficiency.

16 Claims, 7 Drawing Sheets

(52) U.S. Cl.
CPC .............. *A61B 2018/00601* (2013.01); *A61B 2018/00648* (2013.01); *A61B 2018/00666* (2013.01); *A61B 2018/00702* (2013.01); *A61B 2018/00708* (2013.01); *A61B 2018/00726* (2013.01); *A61B 2018/00732* (2013.01); *A61B 2018/00779* (2013.01); *A61B 2018/00827* (2013.01); *A61B 2018/00875* (2013.01); *A61B 2018/00892* (2013.01); *A61B 2018/1266* (2013.01)

(58) Field of Classification Search
CPC ........... A61B 2018/00648; A61B 2018/00666; A61B 2018/00702; A61B 2018/00708; A61B 2018/00726; A61B 2018/00732; A61B 2018/00779; A61B 2018/00827; A61B 2018/00875; A61B 2018/00892; A61B 2018/1266
See application file for complete search history.

(56) References Cited

U.S. PATENT DOCUMENTS

| | | | |
|---|---|---|---|
| 4,658,819 A * | 4/1987 | Harris | A61B 18/1206 606/34 |
| 5,540,681 A * | 7/1996 | Strul | A61B 18/1206 606/1 |
| 5,749,869 A | 5/1998 | Lindenmeier et al. | |
| 5,792,138 A * | 8/1998 | Shipp | A61B 18/12 429/61 |
| 5,836,943 A * | 11/1998 | Miller, III | A61B 18/1206 606/34 |
| D574,323 S | 8/2008 | Waaler | |
| 2004/0167508 A1 | 8/2004 | Wham et al. | |
| 2006/0155270 A1 | 7/2006 | Hancock et al. | |
| 2006/0241589 A1* | 10/2006 | Heim | A61B 18/1402 606/48 |
| 2007/0173811 A1* | 7/2007 | Couture | A61B 18/1445 606/39 |
| 2007/0179490 A1* | 8/2007 | Azar | A61B 18/10 606/28 |
| 2008/0234574 A1 | 9/2008 | Hancock et al. | |
| 2010/0137854 A1 | 6/2010 | Hosier | |
| 2010/0286686 A1 | 11/2010 | Hancock | |
| 2012/0215216 A1 | 8/2012 | Friedrichs et al. | |
| 2013/0035679 A1 | 2/2013 | Orszulak | |
| 2013/0053840 A1 | 2/2013 | Krapohl et al. | |
| 2013/0066311 A1 | 3/2013 | Smith et al. | |
| 2013/0067725 A1 | 3/2013 | Behnke, II et al. | |
| 2013/0072920 A1 | 3/2013 | Behnke, II et al. | |
| 2013/0072921 A1 | 3/2013 | Behnke, II et al. | |
| 2013/0072922 A1 | 3/2013 | Behnke, II et al. | |
| 2013/0072923 A1 | 3/2013 | Behnke, II et al. | |
| 2013/0079673 A1 | 3/2013 | Stein et al. | |
| 2013/0103023 A1 | 4/2013 | Monson et al. | |
| 2013/0190751 A1 | 7/2013 | Brannan | |
| 2013/0193952 A1 | 8/2013 | Krapohl | |
| 2013/0197510 A1 | 8/2013 | Heckel | |
| 2013/0197874 A1 | 8/2013 | Heckel | |
| 2013/0249721 A1 | 9/2013 | Smith | |
| 2013/0253501 A1 | 9/2013 | Joseph | |
| 2013/0261616 A1 | 10/2013 | Prakash et al. | |
| 2013/0267944 A1 | 10/2013 | Krapohl | |
| 2013/0274729 A1 | 10/2013 | Orszulak | |
| 2013/0304049 A1 | 11/2013 | Behnke, II et al. | |
| 2013/0345696 A1 | 12/2013 | Behnke, II et al. | |
| 2014/0002056 A1 | 1/2014 | Moul et al. | |
| 2014/0015535 A1 | 1/2014 | Lopez | |
| 2014/0025064 A1 | 1/2014 | Collins et al. | |
| 2014/0159703 A1 | 6/2014 | Krapohl | |
| 2014/0163431 A1 | 6/2014 | Orszulak et al. | |
| 2014/0171935 A1 | 6/2014 | Digmann et al. | |
| 2014/0180275 A1 | 6/2014 | Weinberg et al. | |
| 2014/0253140 A1 | 9/2014 | Gilbert | |
| 2014/0254221 A1 | 9/2014 | Johnson et al. | |
| 2014/0258800 A1 | 9/2014 | Gilbert | |
| 2014/0276749 A1 | 9/2014 | Johnson | |
| 2014/0276750 A1 | 9/2014 | Gilbert | |
| 2014/0276753 A1 | 9/2014 | Wham et al. | |
| 2014/0276754 A1 | 9/2014 | Gilbert et al. | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1366724 A1 | 12/2003 |
| EP | 1776929 A1 | 4/2007 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| JP | 63 005876 A | 1/1988 |
| JP | 2002-065690 A | 3/2002 |
| JP | 2005-185657 A | 7/2005 |
| SU | 166452 | 1/1965 |
| SU | 727201 A2 | 4/1980 |
| WO | 02/11634 A1 | 2/2002 |
| WO | 02/45589 A2 | 6/2002 |
| WO | 2003/090635 A1 | 11/2003 |
| WO | 2005/115235 A1 | 12/2005 |
| WO | 2006/050888 A1 | 5/2006 |
| WO | 2008/053532 A1 | 5/2008 |
| WO | 2012/076844 A1 | 6/2012 |

OTHER PUBLICATIONS

Wald et al., "Accidental Burns", JAMA, Aug. 16, 1971, vol. 217, No. 7, pp. 916-921.

Vallfors et al., "Automatically Controlled Bipolar Electrosoagulation—'COA-COMP'", Neurosurgical Review 7:2-3 (1984) pp. 187-190.

(56) References Cited

OTHER PUBLICATIONS

Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. Mi, Jan. Mar. 1964, pp. 16-27.
Cosman et al., "Methods of Making Nervous System Lesions", in William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
U.S. Appl. No. 10/406,690, filed Apr. 3, 2003 inventor: Behnke.
U.S. Appl. No. 10/573,713, filed Mar. 28, 2006 inventor: Wham.
U.S. Appl. No. 11/242,458, filed Oct. 3, 2005 inventor: Becker.
U.S. Appl. No. 14/174,551, filed Feb. 6, 2014 inventor: Johnson.
U.S. Appl. No. 14/174,607, filed Feb. 6, 2014 inventor: Friedrichs.
U.S. Appl. No. 14/179,724, filed Feb. 13, 2014 inventor: Johnson.
U.S. Appl. No. 14/180,965, filed Feb. 14, 2014 inventor: Larson.
U.S. Appl. No. 14/181,114, filed Feb. 14, 2014 inventor: Larson.
U.S. Appl. No. 14/190,830, filed Feb. 26, 2014 inventor: Johnson.
U.S. Appl. No. 14/255,051, filed Apr. 17, 2014 inventor: Coulson.
European Search Report issued in corresponding EP application No. 14178300, dated Dec. 19, 2014, 6 pages.
European Search Report issued in corresponding Application No. 16201648, dated Apr. 5, 2017, 7 pages.

* cited by examiner

SYSTEMS AND METHODS FOR IMPROVING EFFICIENCY OF ELECTROSURGICAL GENERATORS

CROSS-REFERENCE TO RELATED APPLICATION

The present application claims the benefit of and priority to U.S. Provisional Application Nos. 61/881,547 and 61/881,575, both filed on Sep. 24, 2013, the entire contents of which are hereby incorporated herein by reference. The present application is related to U.S. patent application Ser. No. 14/320,762, filed on Jul. 1, 2014.

BACKGROUND

1. Technical Field

The present disclosure relates to electrosurgery. More particularly, the present disclosure relates to systems and methods for improving efficiency of electrosurgical generators.

2. Background of Related Art

Electrosurgery involves the application of high-frequency electric current to cut or modify biological tissue during an electrosurgical procedure. Electrosurgery is performed using an electrosurgical generator, an active electrode, and a return electrode. The electrosurgical generator (also referred to as a power supply or waveform generator) generates an alternating current (AC), which is applied to a patient's tissue through the active electrode and is returned to the electrosurgical generator through the return electrode. The AC typically has a frequency above 100 kilohertz (kHz) to avoid muscle and/or nerve stimulation.

During electrosurgery, the AC generated by the electrosurgical generator is conducted through tissue disposed between the active and return electrodes. The tissue's impedance converts the electrical energy (also referred to as electrosurgical energy) associated with the AC into heat, which causes the tissue temperature to rise. The electrosurgical generator controls the heating of the tissue by controlling the electric power (i.e., electrical energy per time) provided to the tissue. Although many other variables affect the total heating of the tissue, increased current density usually leads to increased heating. The electrosurgical energy is typically used for cutting, dissecting, ablating, coagulating, and/or sealing tissue.

The two basic types of electrosurgery employed are monopolar and bipolar electrosurgery. Both of these types of electrosurgery use an active electrode and a return electrode. In bipolar electrosurgery, the surgical instrument includes an active electrode and a return electrode on the same instrument or in very close proximity to one another, usually causing current to flow through a small amount of tissue. In monopolar electrosurgery, the return electrode is located elsewhere on the patient's body and is typically not a part of the electrosurgical instrument itself. In monopolar electrosurgery, the return electrode is part of a device usually referred to as a return pad.

Some electrosurgical generators include a controller that controls the power delivered to the tissue over some period of time based upon measurements of the voltage and current near the output of the electrosurgical generator. These generators use a discrete Fourier transform (DFT) or polyphase demodulation to calculate the phase difference between measurements of the voltage and current for calculating real power and for performing calibration and compensation.

However, at low power levels, some electrosurgical generators exhibit low efficiencies. Thus, there is a need for improved methods of maintaining the efficiency of electrosurgical generators.

SUMMARY

A method for controlling an output of an electrosurgical generator includes the steps of converting a direct current (DC) to an alternating current (AC) using an inverter, and sensing a current and a voltage at an output of the inverter. The method further includes the steps of determining a power level based on the sensed voltage and the sensed current, determining an efficiency of the electrosurgical generator, and inserting a predetermined integer number of off cycles when the efficiency of the electrosurgical generator reaches a threshold power efficiency.

According to a further aspect of the present disclosure, an electrosurgical generator includes a radio frequency (RF) amplifier coupled to an electrical energy source and configured to generate electrosurgical energy, the RF amplifier including: an inverter configured to convert a direct current (DC) to an alternating current. The electrosurgical generator further includes a plurality of sensors configured to sense voltage and current of the generated electrosurgical energy and a controller coupled to the RF amplifier and the plurality of sensors. The generator may further determine a power level based on the sensed voltage and the sensed current, determine an efficiency of the electrosurgical generator, and insert a predetermined integer number of off cycles when the efficiency of the electrosurgical generator reaches a threshold power efficiency.

According to another aspect of the present disclosure a method of improving efficiency of an electrosurgical generator includes determining power levels based on sensed voltage and sensed current, determining an efficiency of the electrosurgical generator based on the detected power levels, and gradually dropping a predetermined integer number of output or off cycles when the efficiency of the electrosurgical generator reaches a threshold power efficiency, the predetermined integer number of output or off cycles being randomized via a random number generator.

According to a further aspect of the present disclosure, an electrosurgical generator includes a radio frequency (RF) amplifier having an inverter configured to convert a direct current (DC) to an alternating current (AC), a plurality of sensors configured to sense voltage and current of generated electrosurgical energy, and a controller coupled to the RF amplifier and the plurality of sensors. The generator may further determine a power level based on sensed voltage and sensed current, determine an efficiency of the electrosurgical generator based on the detected power level, and gradually drop a predetermined integer number of off cycles when the efficiency of the electrosurgical generator reaches a threshold power efficiency, the predetermined integer number of off cycles being randomized via a random number generator.

BRIEF DESCRIPTION OF THE DRAWINGS

Various embodiments of the present disclosure are described with reference to the accompanying drawings wherein.

DETAILED DESCRIPTION

Figure 1:
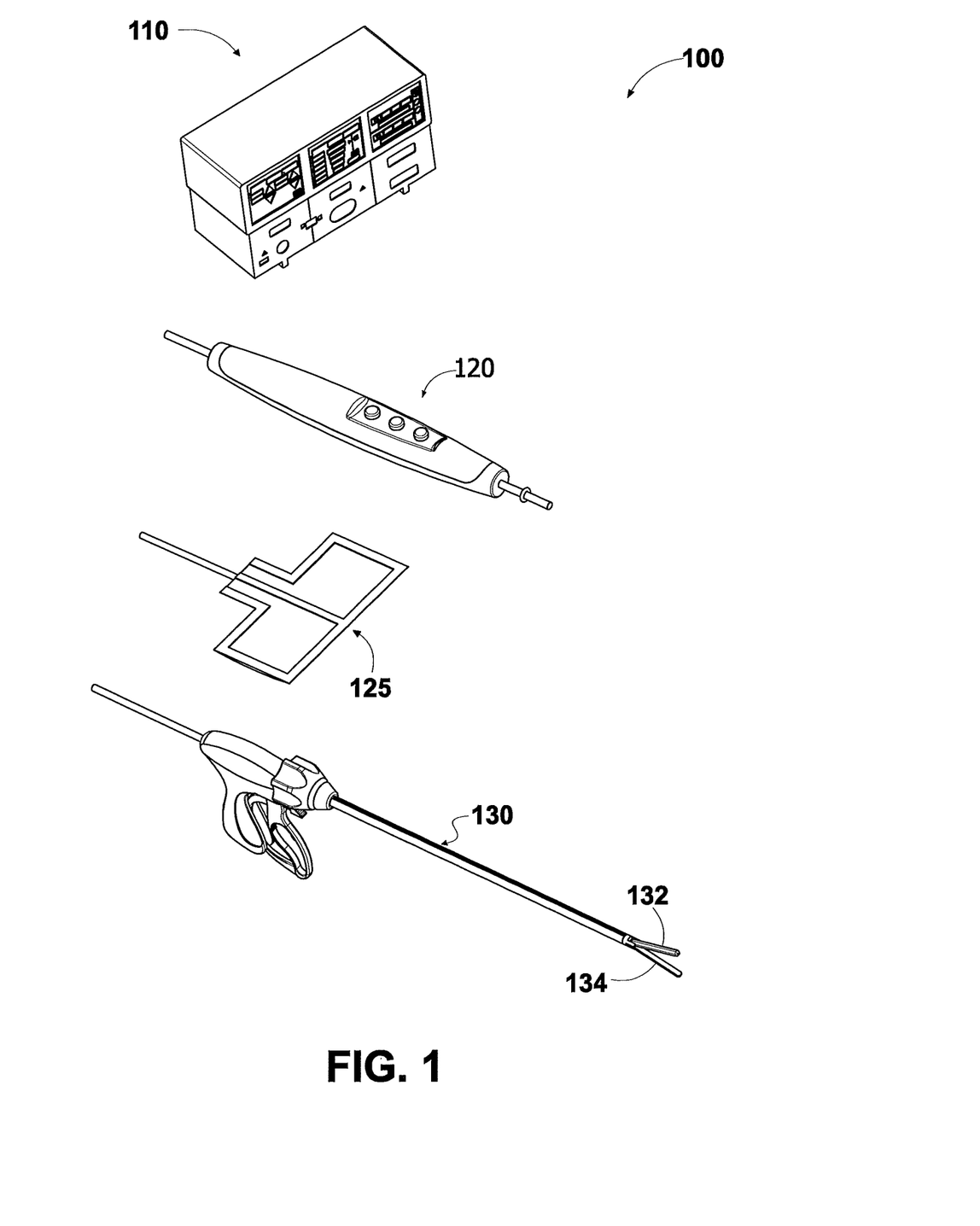
FIG. 1 is an illustration of an electrosurgical system including a generator, in accordance with embodiments of the present disclosure.

FIG. 1 illustrates an electrosurgical system 100 in accordance with embodiments of the present disclosure. The electrosurgical system 100 includes an electrosurgical generator 110 which generates electrosurgical energy to treat tissue of a patient. The electrosurgical generator 110 generates an appropriate level of electrosurgical energy based on the selected mode of operation (e.g., cutting, coagulating, ablating, or sealing) and/or the sensed voltage and current waveforms of the electrosurgical energy. The electrosurgical system 100 may also include a plurality of output connectors corresponding to a variety of electrosurgical instruments.

The electrosurgical system 100 further includes a monopolar electrosurgical instrument 120 having an electrode for treating tissue of the patient (e.g., an electrosurgical cutting probe or ablation electrode) with a return pad 125. The monopolar electrosurgical instrument 120 can be connected to the electrosurgical generator 110 via one of the plurality of output connectors. The electrosurgical generator 110 may generate electrosurgical energy in the form of radio frequency (RF) energy. The electrosurgical energy is supplied to the monopolar electrosurgical instrument 120, which applies the electrosurgical energy to treat the tissue. The electrosurgical energy is returned to the electrosurgical generator 110 through the return pad 125. The return pad 125 provides a sufficient contact area with the patient's tissue so as to minimize the risk of tissue damage due to the electrosurgical energy applied to the tissue. In addition, the electrosurgical generator 110 and the return pad 125 may be configured to monitor tissue-to-patient contact to ensure that sufficient contact exists between the return pad 125 and the patient to minimize the risk of tissue damages.

The electrosurgical system 100 also includes a bipolar electrosurgical instrument 130, which can be connected to the electrosurgical generator 110 via one of the plurality of output connectors. During operation of the bipolar electrosurgical instrument, electrosurgical energy is supplied to one of the two jaw members, e.g., jaw member 132, of the instrument's forceps, is applied to treat the tissue, and is returned to the electrosurgical generator 110 through the other jaw member, e.g., jaw member 134.

The electrosurgical generator 110 may be any suitable type of generator and may include a plurality of connectors to accommodate various types of electrosurgical instruments (e.g., monopolar electrosurgical instrument 120 and bipolar electrosurgical instrument 130). The electrosurgical generator 110 may also be configured to operate in a variety of modes, such as ablation, cutting, coagulation, and sealing. The electrosurgical generator 110 may include a switching mechanism (e.g., relays) to switch the supply of RF energy among the connectors to which various electrosurgical instruments may be connected. For example, when an electrosurgical instrument 120 is connected to the electrosurgical generator 110, the switching mechanism switches the supply of RF energy to the monopolar plug. In embodiments, the electrosurgical generator 110 may be configured to provide RF energy to a plurality of instruments simultaneously.

The electrosurgical generator 110 includes a user interface having suitable user controls (e.g., buttons, activators, switches, or touch screens) for providing control parameters to the electrosurgical generator 110. These controls allow the user to adjust parameters of the electrosurgical energy (e.g., the power level or the shape of the output waveform) so that the electrosurgical energy is suitable for a particular surgical procedure (e.g., coagulating, ablating, tissue sealing, or cutting). The electrosurgical instruments 120 and 130 may also include a plurality of user controls. In addition, the electrosurgical generator 110 may include one or more display screens for displaying a variety of information related to operation of the electrosurgical generator 110 (e.g., intensity settings and treatment complete indicators). The electrosurgical instruments 120 and 130 may also include a plurality of input controls that may be redundant with certain input controls of the electrosurgical generator 110. Placing the input controls at the electrosurgical instruments 120 and 130 allows for easier and faster modification of the electrosurgical energy parameters during the surgical procedure without requiring interaction with the electrosurgical generator 110.

Figure 2A:
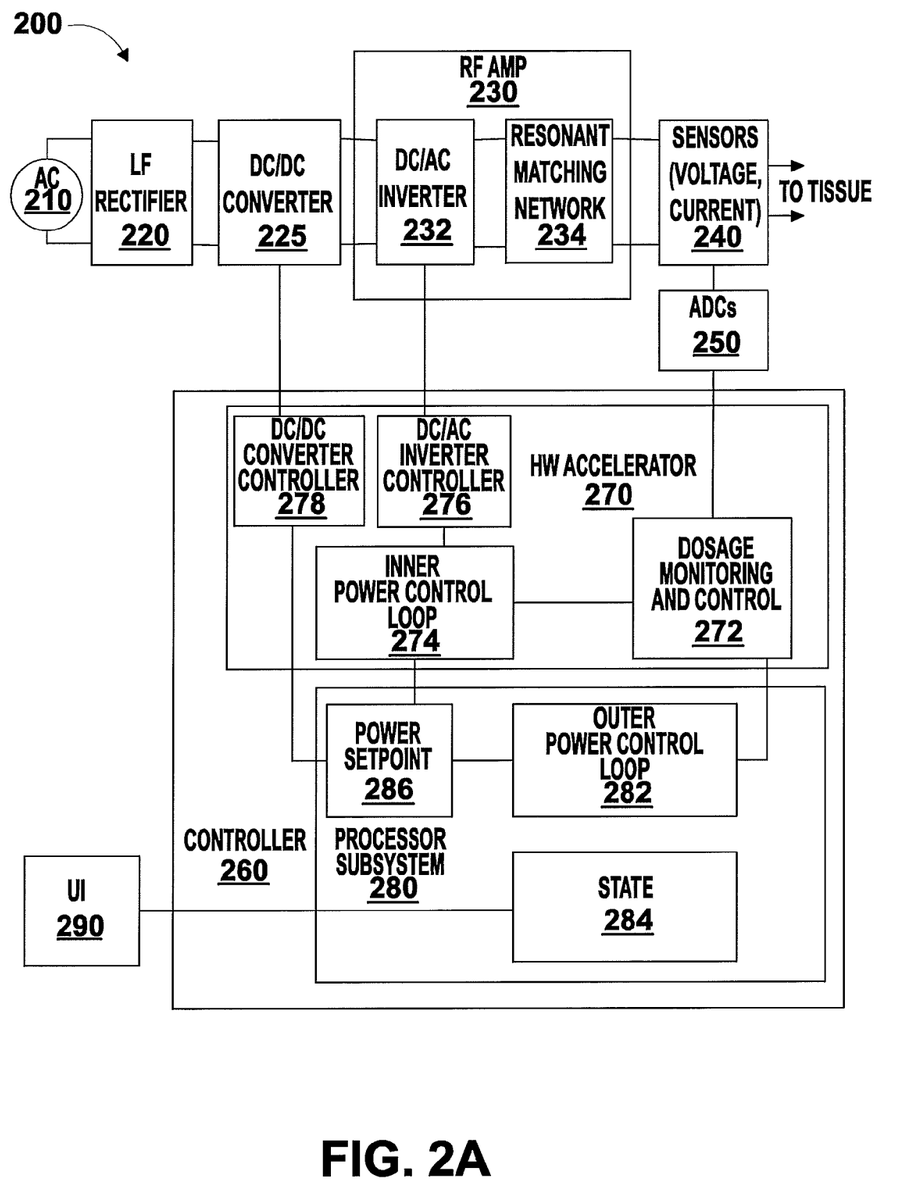
FIG. 2A is a block diagram of an electrosurgical system including generator circuitry according to a combination of a modified-Kahn technique and a Class S generator topology, in accordance with one embodiment of the present disclosure.

FIG. 2A is a block diagram of generator circuitry 200 within the electrosurgical generator of FIG. 1. The generator circuitry 200 includes a low frequency (LF) rectifier 220, a direct current-to-direct current (DC/DC) converter 225, an RF amplifier 230, a plurality of sensors 240, analog-to-digital converters (ADCs) 250, a controller 260, a hardware accelerator 270, a processor subsystem 280, and a user interface (UI) 290. The generator circuitry 200 is configured to connect to a power source 210, such as a wall power outlet or other power outlet, which generates alternating current (AC) having a low frequency (e.g., 25 Hz, 50 Hz, or 60 Hz). The power source 210 provides the AC power to the LF rectifier 220, which converts the AC to direct current (DC). Alternatively, the power source 210 and the LF rectifier 220 may be replaced by a battery or other suitable device to provide DC power.

The DC output from the LF rectifier 220 is provided to the DC/DC converter 225 which converts the DC to a desired level. The converted DC is provided to the RF amplifier 230, which includes a DC-to-AC (DC/AC) inverter 232 and a resonant matching network 234. The DC/AC inverter 232 converts the converted DC to an AC waveform having a frequency suitable for an electrosurgical procedure (e.g., 472 kHz, 29.5 kHz, and 19.7 kHz).

The appropriate frequency for the electrosurgical energy may differ based on electrosurgical procedures and modes of electrosurgery. For example, nerve and muscle stimulations cease at about 100,000 cycles per second (100 kHz) above which point some electrosurgical procedures can be performed safely, i.e., the electrosurgical energy can pass through a patient to targeted tissue with minimal neuromuscular stimulation. For example, typically, ablation procedures use a frequency of 472 kHz. Other electrosurgical procedures can be performed at pulsed rates lower than 100 kHz, e.g., 29.5 kHz or 19.7 kHz, with minimal risk of damaging nerves and muscles, e.g., Fulgurate or Spray. The DC/AC inverter 232 can output AC signals with various frequencies suitable for electrosurgical operations.

As described above, the RF amplifier 230 includes a resonant matching network 234. The resonant matching network 234 is coupled to the output of the DC/AC inverter 232 to match the impedance at the DC/AC inverter 232 to the impedance of the tissue so that there is maximum or optimal power transfer between the generator circuitry 200 and the tissue.

Figure 2B:
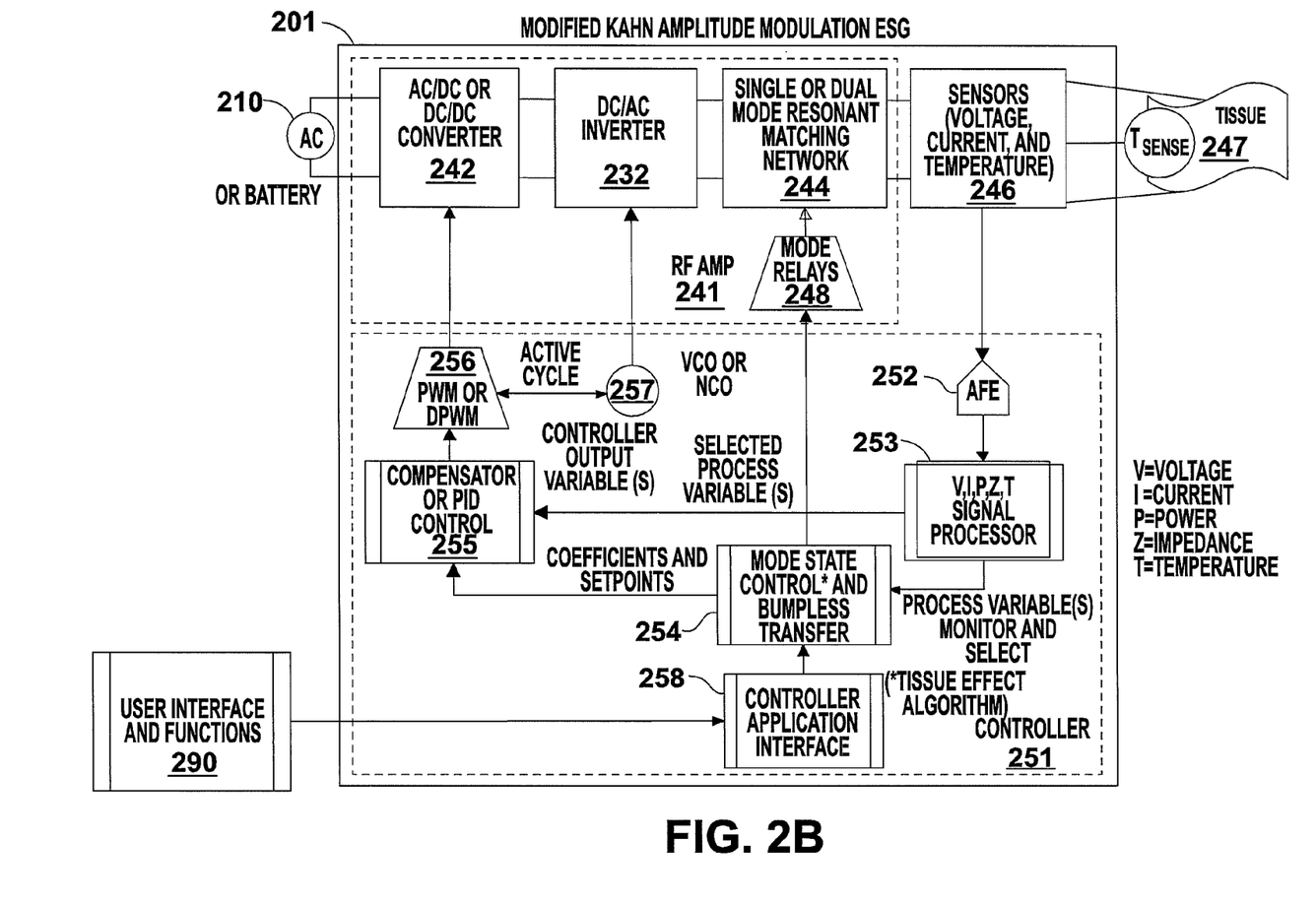
FIG. 2B is a block diagram of an electrosurgical system including generator circuitry according to the modified-Kahn technique, in accordance with another embodiment of the present disclosure.
Figure 2C:
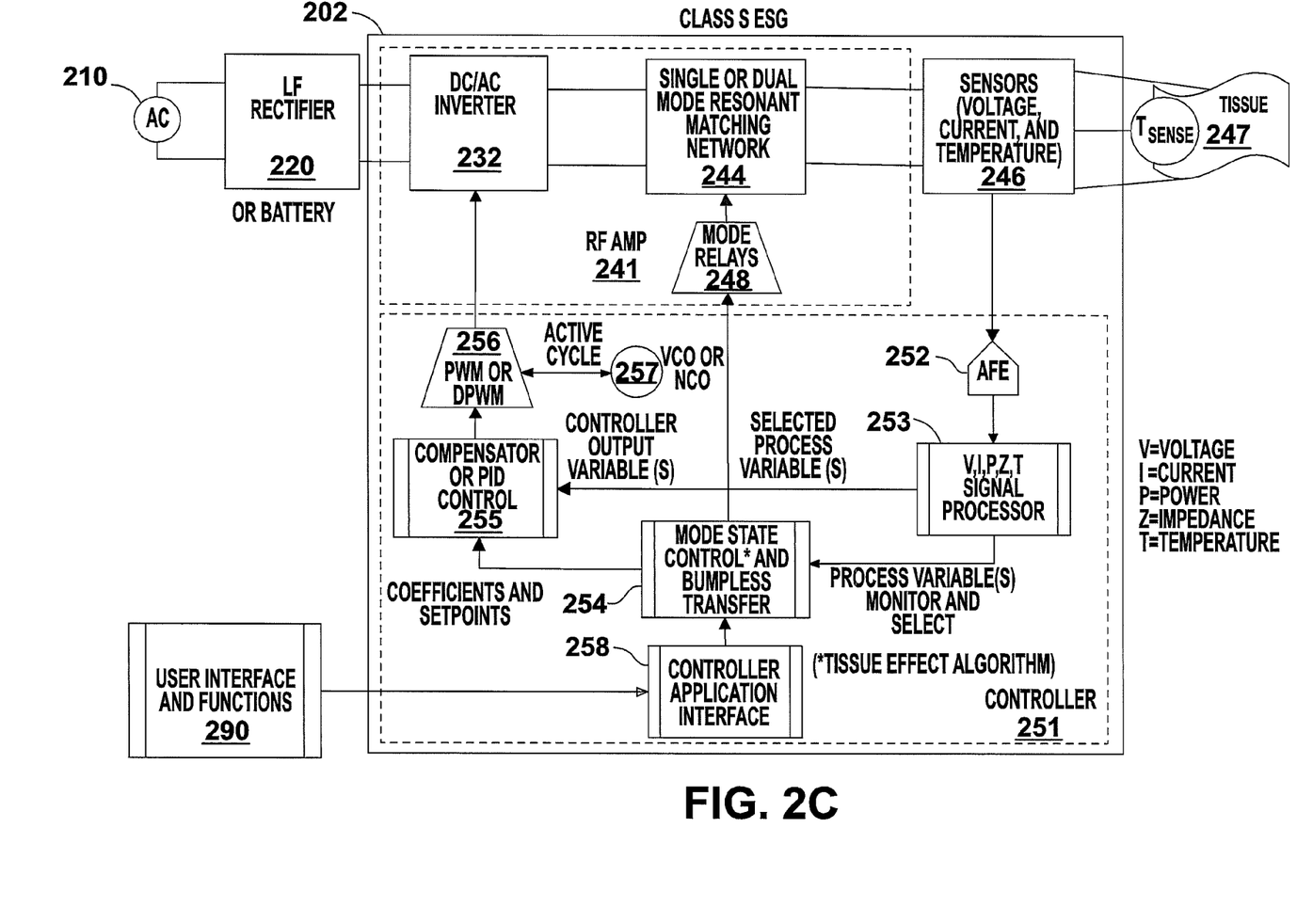
FIG. 2C is a block diagram of an electrosurgical system including generator circuitry according to the Class S device topology, in accordance with still another embodiment of the present disclosure.

The electrosurgical energy provided by the DC/AC inverter 232 of the RF amplifier 230 is controlled by the controller 260. The voltage and current waveforms of the electrosurgical energy output from the DC/AC inverter 232 are sensed by the plurality of sensors 240 and provided to the controller 260, which generates control signals from a DC/DC converter controller 278, e.g., a pulse width modulator (PWM) or digital pulse width modulator (DPWM) to control the output of the DC/DC converter 225 and from a DC/AC inverter controller 276 to control the output of the DC/AC inverter 232. The controller 260 also receives input signals via the user interface (UI) 290. The UI 290 allows a user to select a type of electrosurgical procedure (e.g., monopolar or bipolar) and a mode (e.g., coagulation, ablation, sealing, or cutting), or input desired control parameters for the electrosurgical procedure or the mode. The DC/DC converter 225 of FIG. 2A may be fixed or variable depending on the power setting or desired surgical effects. When it is fixed, the RF amplifier behaves as a Class S device, which is shown in FIG. 2C. When it is variable, it behaves as a device according to the modified-Kahn technique, which is shown in FIG. 2B.

The plurality of sensors 240 sense voltage and current at the output of the RF amplifier 230. The plurality of sensors 240 may include two or more pairs or sets of voltage and current sensors that provide redundant measurements of the voltage and current. This redundancy ensures the reliability, accuracy, and stability of the voltage and current measurements at the output of the RF amplifier 230. In embodiments, the plurality of sensors 240 may include fewer or more sets of voltage and current sensors depending on the application or the design requirements. The plurality of sensors 240 may also measure the voltage and current output from other components of the generator circuitry 200 such as the DC/AC inverter 232 or the resonant matching network 234. The plurality of sensors 240 may include any known technology for measuring voltage and current including, for example, a Rogowski coil.

The sensed voltage and current waveforms are fed to analog-to-digital converters (ADCs) 250. The ADCs 250 sample the sensed voltage and current waveforms to obtain digital samples of the voltage and current waveforms. This is also often referred to as an Analog Front End (AFE). The digital samples of the voltage and current waveforms are processed by the controller 260 and used to generate control signals to control the DC/AC inverter 232 of the RF amplifier 230 and the DC/DC converter 225. The ADCs 250 may be configured to sample the sensed voltage and current waveforms at a sample frequency that is an integer multiple of the RF frequency.

As shown in the embodiment of FIG. 2A, the controller 260 includes a hardware accelerator 270 and a processor subsystem 280. As described above, the controller 260 is also coupled to a UI 290, which receives input commands from a user and displays output and input information related to characteristics of the electrosurgical energy (e.g., selected power level). The hardware accelerator 270 processes the output from the ADCs 250 and cooperates with the processor subsystem 280 to generate control signals.

The hardware accelerator 270 includes a dosage monitoring and control (DMAC) 272, an inner power control loop 274, a DC/AC inverter controller 276, and a DC/DC converter controller 278. All or a portion of the controller 260 may be implemented by a field programmable gate array (FPGA), an application specific integrated circuit (ASIC), a digital signal processor (DSP), and/or a microcontroller.

The DMAC 272 receives samples of the sensed voltage and current waveforms from the ADCs 250 and calculates the average real power and the real part of the tissue impedance. The DMAC 272 then provides the real power and the real part of the impedance of the tissue to the inner power control loop 274, which generates a control signal for the DC/AC inverter controller 276 based on one or more of the real power and the real part of the impedance of the tissue. The DC/AC inverter controller 276 in turn generates a first pulse-width modulation (PWM) control signal to control the output of the DC/AC inverter 232.

The processor subsystem 280 includes an outer power control loop 282, a state machine 284, and a power setpoint circuit 286. The processor subsystem 280 generates a second PWM control signal based on the output of the DMAC 272 and parameters (e.g., electrosurgical mode) selected by the user via the UI 290. Specifically, the parameters selected by the user are provided to the state machine 284 which determines a state or mode of the generator circuitry 200. The outer power control loop 282 uses this state information and the output from the DMAC 272 to determine control data. The control data is provided to the power setpoint circuit 286, which generates a power setpoint based on the control data. The DC/DC converter controller 278 uses the power setpoint to generate an appropriate PWM control signal for controlling the DC/DC converter 225 to converter the DC output from the LF rectifier 220 to a desired level. If the user does not provide operational parameters to the state machine 284 via the UI 290, then the state machine 284 may maintain or enter a default state.

Figure 3:
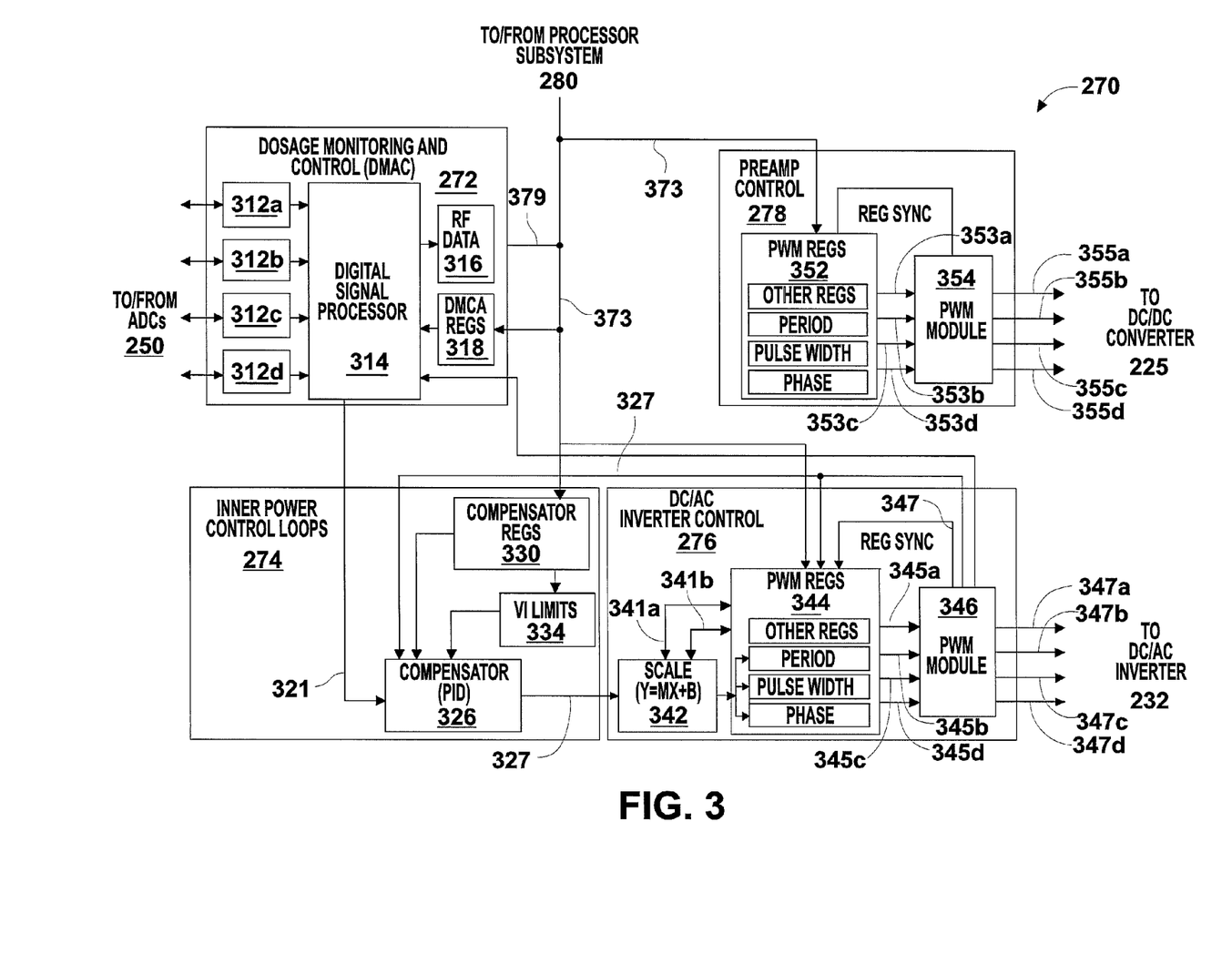
FIG. 3 a schematic block diagram of a controller of the generator circuitry of FIG. 2A, in accordance with an embodiment of the present disclosure.

FIG. 3 shows a more detailed diagram of the hardware accelerator 270 of FIG. 2A. The hardware accelerator 270 implements those functions of the generator circuitry 200 that may have special processing requirements such as high processing speeds. The hardware accelerator 270 includes the DMAC 272, the inner power loop control 274, the DC/AC inverter controller 276, and the DC/DC converter controller 278 shown in FIG. 2A.

The DMAC 272 includes four analog-to-digital converter (ADC) controllers 312a-312d, a digital signal processor 314, RF data registers 316, and DMAC registers 318. The ADC controllers 312a-312d control the operation of the ADCs 250 (FIG. 2A), which convert sensed voltage and current waveforms into digital data. The digital data is then provided to the digital signal processor 314 that implements various filtering and other digital signal processing functions.

The sensed voltage and current are the digital input to the ADCs 250, which sample the sensed voltage and current. The ADC controllers 312a-312d provide operational parameters, including a predetermined sampling rate, to the ADCs 250 so that the ADCs sample the sensed voltage and current synchronously at a predetermined sampling rate, i.e., a predetermined number of samples per second, or predetermined sampling period that is coherent with the RF inverter frequency, i.e., an integer multiple sampling frequency to the RF inverter frequency. The ADC controllers 312a-312d control the operation of the ADCs 250, which convert sensed voltage and current waveforms into digital data. The digital data is then provided to the digital signal processor 314 that implements various filtering and other digital signal processing functions.

The sensed voltage and current are input to the ADCs 250, which sample the sensed voltage and current. The ADC controllers 312a-312d provide operational parameters, including a predetermined sampling rate, to the ADCs 250 so that the ADCs sample the sensed voltage and current synchronously at a predetermined sampling rate, i.e., a predetermined number of samples per second, or predetermined sampling period. The ADC controllers 312a-312d may be configured to control the ADCs 250 so that the sampling period corresponds to an integer multiple of the RF frequency of the voltage and current waveforms. This is often referred to as coherent sampling.

The digital data obtained by sampling the voltage and current waveforms is provided to the digital signal processor 314 via the ADC controllers 312a-312d. The digital signal processor 314 uses the digital data to calculate a complex voltage $V_{comp}$, a complex current $I_{comp}$, a real power $P_{real}$, and a real part of the tissue impedance $Z_{real}$. Generally, tissue impedance is real or resistive, but can have a small capacitive component after the tissue is "cooked." Further, a cable between the electrosurgical generator and the tissue also has resistive and reactive components. For these reasons, electrosurgical generators typically include controls systems that compensate for these parasitics to more accurately measure the tissue impedance. These control systems, however, require complex computations that are computationally inefficient, which results in additional cost to perform the tissue impedance calculations in a timely manner or at update rates commensurate to the capabilities of the RF control loop calculations.

In alternative embodiments depicted in FIGS. 2B and 2C, the hardware accelerator is not available and many of the primary RF measurement and control functions just described reside instead entirely within a programmable device called an application specific standard product (ASSP) integrated circuit that includes at least a DSP core processor and multiple digital pulse width modulators (DPWM) that are substantially similar in function to the hardware accelerator and its DSP and/or microcontroller core.

In other embodiments, there may also be a second microprocessor core available within the ASSP that contains additional ADCs which may be connected to the sensors for performing the redundant dosage monitoring functions separately from the RF control functions. The second processor may also perform user interface functions such as receiving and requesting power settings, activation requests, and so forth for the user from the RF controller. The ASSP may also utilize only one RF control loop (or compensator loop), instead of two "inner" and "outer" compensator loops, for controlling directly any of the following: power, voltage, current, temperature, or impedance. This loop may use a single proportional-integral-derivative compensator that changes between these process variables using bumpless transfer methods and saturable limits.

FIG. 2B shows an electrosurgical system including generator circuitry according to the modified-Kahn technique 201. The generator circuitry 201 includes an RF amplifier 241 and a controller 251 for controlling the RF amplifier 241 to deliver electrosurgical energy having desired characteristics to tissue 247 being treated. The RF amplifier 241 receives AC or DC from the power source 210. The RF amplifier includes an AC/DC or DC/DC converter 242, which converts the AC or DC provided by the power source 210 into a suitable level of DC. As in FIG. 2A, the RF amplifier 241 also includes a DC/AC inverter 232 which converts the DC to AC. The RF amplifier 241 also includes a single- or dual-mode resonant matching network 244 and mode relays 248 for switching modes of the resonant matching network 244.

The output from the RF amplifier 241 is provided to sensors 246, which may include voltage sensors, current sensors, and temperature sensors. The sensor signals output from sensors 246 are provided to the controller 251 via an analog front end (AFE) 252 of the controller 251. The AFE conditions and samples the sensor signals to obtain digital sensor data representing the sensor signals. The controller 251 also includes a signal processor 253, a mode state control and bumpless transfer unit 254, a compensator or PID controller 255, a pulse width modulator (PWM) or digital pulse width modulator (DPWM) 256, and a voltage-controlled oscillator or numerically-controlled oscillator 257.

The signal processor 253 receives the digital sensor data and performs the calculations and other functions of the systems and methods according to the present disclosure. Among other things, the signal processor 253 calculates the real and imaginary parts of the sensed voltage and current, the impedance, and/or the power, and performs functions to control one or more of the voltage, current, power, impedance, and temperature. The signal processor 253 also generates and provides process variables to the mode state control and bumpless transfer unit 254 and a compensator or PID controller 255. The mode state control and bumpless transfer unit 254 controls the mode relays 248 for the single or dual mode resonant matching network 244 according to the tissue effect algorithm, and generates and provides coefficients and setpoints to the compensator or PID controller 255.

The compensator or PID controller 255 generates controller output variables and provides them to the pulse width modulator (PWM) or digital pulse width modulator (DPWM) 256. The pulse width modulator (PWM) or digital pulse width modulator (DPWM) 256 receives an oscillator signal from the voltage-controlled oscillator or the numerically-controlled oscillator 257 and generates a control signal for controlling the AC/DC or DC/DC converter 242. The voltage-controlled oscillator or the numerically-controlled oscillator 257 also generates control signals for controlling the DC/AC inverter 232.

Like the generator circuitry 200 of FIG. 2A, the generator circuitry 201 includes a user interface 290 through which a user can control and/or monitor the functions of the generator circuitry 201 via a controller application interface 258 of the controller 251.

FIG. 2C shows an electrosurgical system including generator circuitry according to a Class S device topology 202. Unlike the generator circuitry 201 of FIG. 2B, the generator circuitry 202 does not include the AC/DC or DC/DC Converter 242. An external low-frequency (LF) rectifier 220 or battery provides an appropriate level of DC to the DC/AC Inverter 232 of the RF amplifier 241. As shown in FIG. 2C, the PWM or DPWM 256 receives an oscillator signal from the VCO or NCO 257 and generates a control signal for controlling the DC/AC Inverter 232.

The output of the digital signal processor 314 is provided to the processor subsystem 280 of FIG. 2A via RF data registers 316 (see FIG. 3). The DMAC 272 also includes DMAC registers 318 that receive and store relevant parameters for the digital signal processor 314 (see FIG. 3). The digital signal processor 314 further receives signals from a PWM module 346 of the DC/AC inverter controller 276.

The DMAC 272 provides a control signal to the inner power control loop 274 via signal line 321 and to the processor subsystem 280 via signal line 379. The inner power control loop 274 processes the control signal and outputs a control signal to the DC/AC inverter controller 276. The inner power control loop 274 includes a compensator 326, compensator registers 330, and VI limiter 334. The signal line 321 carries and provides a real part of the impedance to the compensator 326.

When there is a user input, the processor subsystem 280 receives the user input and processes it with the outputs from the digital signal processor 314 via a signal line 379. The processor subsystem 280 provides control signals via a compensator registers 330 to a VI limiter 334, which corresponds to the power setpoint circuit 286 in FIG. 2A. The VI limiter 334 then provides a desired power profile (e.g., a minimum and a maximum limits of the power for a set electrosurgical mode or operation) based on the user input and the output of the digital signal processor 314, the compensator registers 330 also provide other control parameters to the compensator 326, and then the compensator 326 combines all control parameters from the compensator registers 330 and the VI limiter 334, to generate output to the DC/AC inverter controller 276 via signal line 327.

The DC/AC inverter controller 276 receives a control parameter and outputs control signals that drives the DC/AC inverter 232. The DC/AC inverter controller 276 includes a scale unit 342, PWM registers 344, and the PWM module 346. The scale unit 342 scales the output of the compensator registers 330 by multiplying and/or adding a number to the output. The scale unit 342 receives a number for multiplication and/or a number for addition from the PWM registers 344 via signal lines, 341a and 341b. The PWM registers 344 store several relevant parameters to control the DC/AC inverter 232, e.g., a period, a pulse width, and a phase of the AC signal to be generated by the DC/AC inverter 232 and other related parameters. The PWM registers 344 send signals 345a-345d to the PWM module 346. The PWM module 346 receives output from the PWM registers 344 and generates four control signals, 347a-347d, that control four transistors of the DC/AC inverter 232 of the RF amplifier 230 in FIG. 2A. The PWM module 346 also synchronizes its information with the information in the PWM registers 344 via a register sync signal 347.

The PWM module 346 further provides control signals to the compensator 326 of the inner power control loop 274. The processor subsystem 280 provides control signals to the PWM module 346. In this way, the DC/AC inverter controller 276 can control the DC/AC inverter 232 of the RF amplifier 230 with integrated internal input (i.e., processed results from the plurality of sensors by the DMAC 272) and external input (i.e., processed results from the user input by the processor subsystem 280).

The processor subsystem 280 also sends the control signals to the DC/DC converter controller 278 via signal line 373. The DC/DC converter controller 278 processes the control signals and generates another control signals so that the DC/DC converter 225 converts direct current to a desired level suitable for being converted by the RF amplifier 230. The DC/DC converter controller 278 includes PWM registers 352 and a PWM module 354. The PWM registers 352 receive outputs from the processor subsystem 280 via signal line 373 and stores relevant parameters as the PWM registers 344 does. The PWM registers 352 send signals 353a-353d to the PWM module 354. The PWM module 354 also sends a register sync signal to the PWM registers 352 and generates four control signals, 355a-355d, that control four transistors of the DC/DC converter 225 in FIG. 2A.

Figure 4:
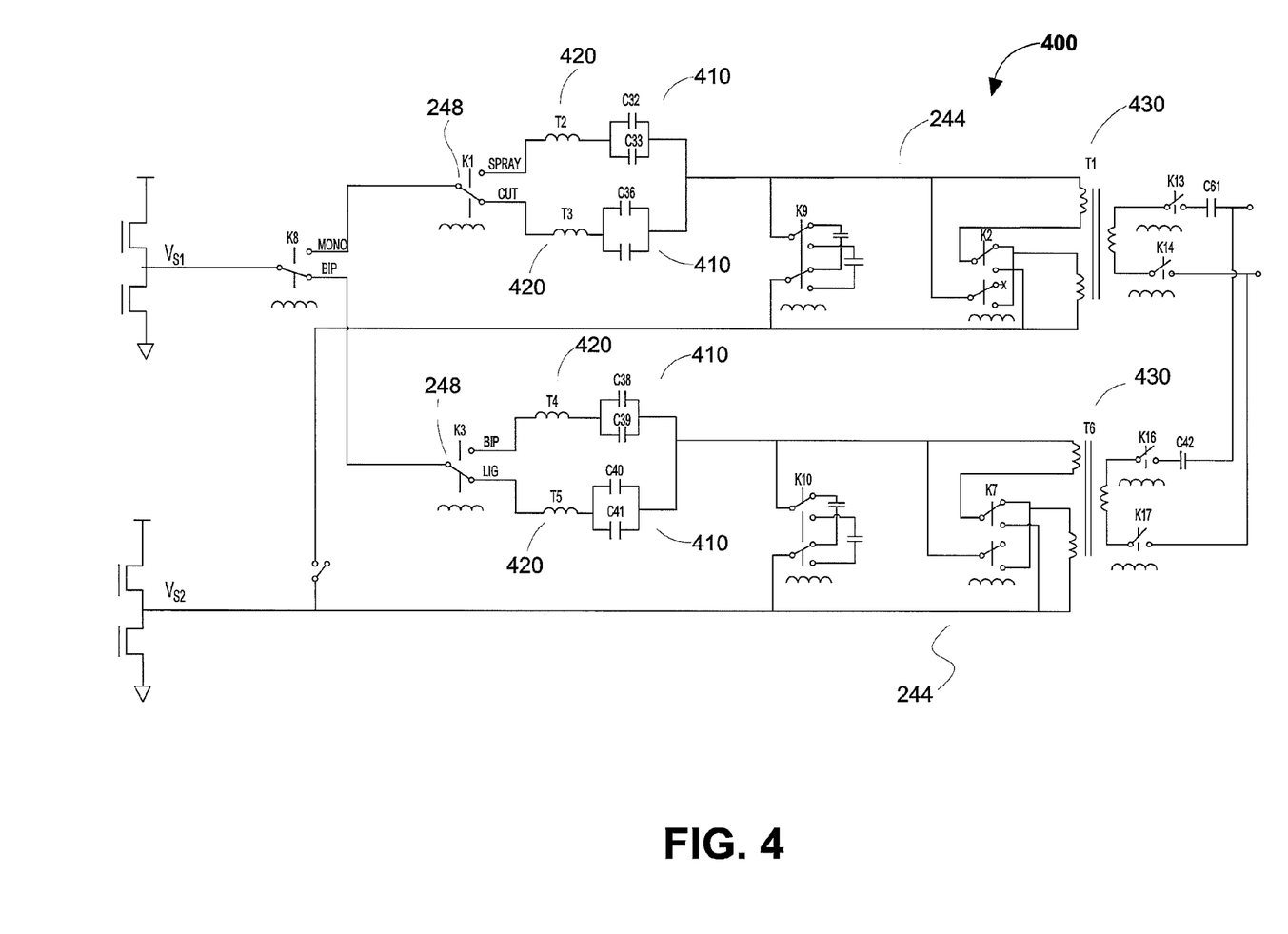
FIG. 4 is a circuit diagram illustrating switching in different resonant components, in accordance with an embodiment of the present disclosure.

FIG. 4 is a circuit diagram 400 illustrating switching in different resonant components, in accordance with an embodiment of the present disclosure. The circuit diagram 400 illustrates mode relays 248 and matching network 244. The mode relays 248 allow a user to switch between different operating modes. For example, the top mode relay 248 allows a user to switch between a cut mode and a spray mode, whereas the bottom mode relay 248 allows a user to switch between a ligature mode and a blend mode. One skilled in the art may contemplate a plurality of relays for switching between a plurality of operating modes. Additionally, the capacitors 410 and the inductors 420 are appropriately sized for the selected mode. The matching network 244 includes two transformers 430 to vary the relative voltage of the circuit 400 and provide for patient isolation.

The preceding description provides a detailed account of the components and devices for controlling the output of an electrosurgical generator 110. Typically, the manner in which average power output from a DC/AC inverter (and then applied to a patient) is reduced is by reducing the pulse width of the PWM signal output by the DC/AC inverter controller 276 (FIG. 2A). However, power control in this manner can result in a loss of efficiency when operating a low power setting.

Figure 5A:
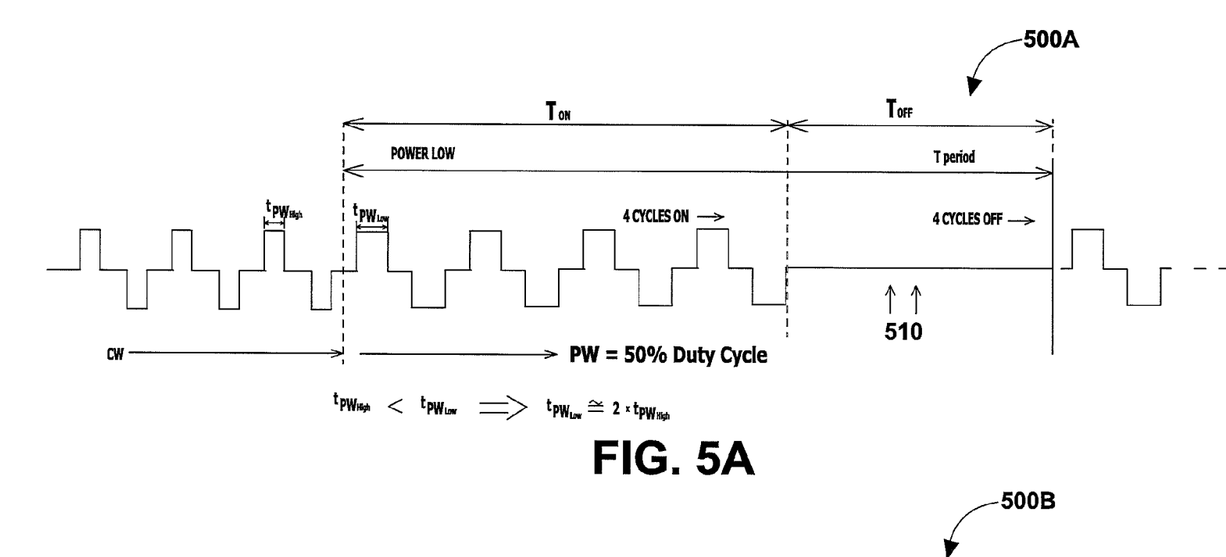
FIGS. 5A and 5B are graphs illustrating insertion of output cycles at predetermined time periods, in accordance with an embodiment of the present disclosure.

FIG. 5A depicts an output signal of the DC/AC inverter controller 276 (FIG. 2A) and particularly the PWM module 346 (FIG. 3), which control the DC/AC inverter 232. In FIG. 5A, the initial signal is a continuous wave (CW) controlling the DC/AC inverter 232. The pulses (i.e., the high and low signals) of the CW have a short pulse width $T_{PW_{High}}$. By shortening the pulse width, the average power output by the DC/AC inverter 232, and ultimately applied to the patient, is reduced. As noted above, however, mere reduction in the pulse width when using a CW can result in efficiency losses as the average power output is reduced.

According to one embodiment of the present disclosure, the efficiency of the DC/AC inverter 232 may be increased by lengthening the pulse width to $T_{PW_{Low}}$, and transitioning from a CW to a pulsed wave (PW) with a 50% duty cycle. In other words, pulses are only sent to the DC/AC inverter 232 during 50% of a period T. In the example of FIG. 5A, during the period T, four cycles of pulsed signals are produced during a period $T_{on}$ followed by no signal being produced for a period $T_{off}$, which is also four cycles, thus $T_{on}$ and $T_{off}$ are equal (i.e., represent the same period of time). Further, in this example, by lengthening the pulse width $T_{PW_{Low}}$ to approximately twice $T_{PW_{High}}$, the average power output by the DC/AC inverter 232 may be maintained. However, because of the decrease in the number of switchings that occur at the DC/AC inverter 232, an increase of the time between such switchings (i.e., $T_{PW_{Low}} > T_{PW_{High}}$), and a period $T_{off}$ where no switchings occur, an increase in efficiency is achieved as compared to simply reducing the pulse width of a CW.

Figure 5B:
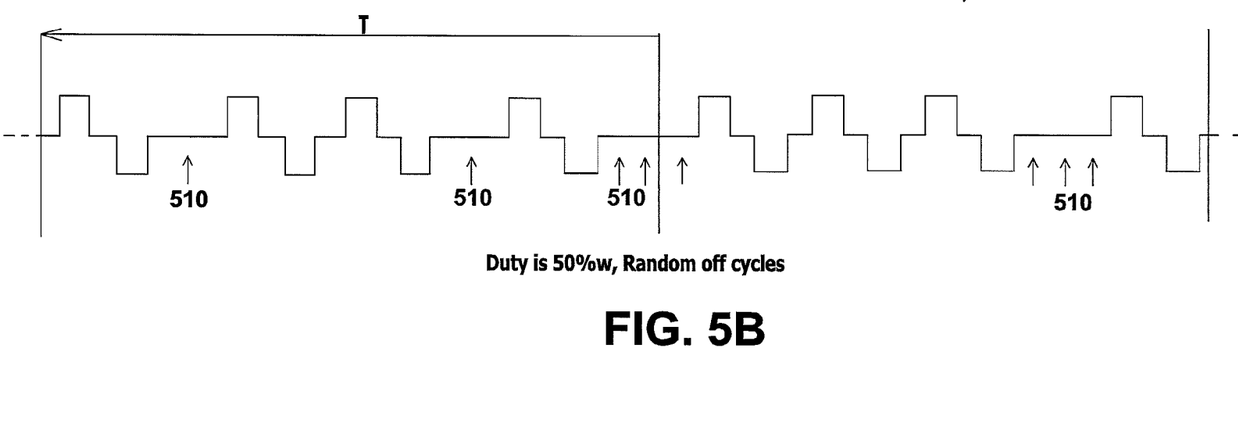

In an alternative or additional embodiment, the efficiency at low power levels may be improved by dropping or deactivating at least some predetermined integer number of output cycles. As shown in FIG. 5B, the duty cycle of the PW which is supplied to the DC/AC inverter 232 remains at 50%. However, rather than a PW where a period $T_{on}$ is followed by a period $T_{off}$ where periods $T_{on}$ and $T_{off}$ are equal, the periods of $T_{off}$ may be randomly dispersed in the period T, as represented by the periods of no signal 510. The aggregate time for the periods of no signal 510 are equivalent to $T_{off}$ (shown in FIG. 5A), and result in the same output from the DC/AC inverter, when the amplitude of the current remains constant.

The result of the signaling schemes depicted in FIGS. 5A and 5B is that two time parameters are employed in achieving a desired average power. The first is the overall duty cycle (shown as 50%) whereby no signal is supplied during $T_{off}$ or half of the period T. The other is the pulse width (e.g., $T_{PW_{Low}}$) of the signal supplied during $T_{on}$, resulting in greater control and greater efficiency when low powers are desired for use by a clinician. As an example, lower power may be 10% of rated power of the electrosurgical generator 110.

It is noted that the efficiency may be determined by the controller 260. However, in certain circumstances, the efficiency may not be determined by the controller 260, but with other external efficiency computing components/elements. Reference is made to U.S. Provisional Patent No. 61/838,753 entitled "DEAD-TIME OPTIMIZATION OF RESONANT INVERTERS," the entire contents of which are hereby incorporated by reference, for alternative online and/or offline methods of determining efficiency. For example, the efficiency of the system may be characterized offline and the off cycles may be inserted when a predetermined threshold is reached for a control parameter, such as, duty cycle or phase, or when a sensed power drops below a certain threshold.

Moreover, the dropped cycles, within any given time period, may be randomized by using a pseudo-random sequence determined by a random number generator. The random number generator may be, for example, a Galois sequence that spreads out the spectrum in order to mitigate any undesirable frequencies. As a result, a useful range of operation of the electrosurgical generator 110 may be extended, while maintaining reasonable energy conversion efficiency.

It is to be understood that the disclosed embodiments are merely exemplary of the disclosure, which can be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Further, the terms and phrases used herein are not intended to be limiting; but rather, to provide an understandable description of the disclosure.

It is to be understood that the terminology used herein is for the purpose of describing particular embodiments only and is not intended to be limiting. In this document, the terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the object being described. Finally, as used herein, the terms "distal" and "proximal" are considered from the vantage of the user or surgeon, thus the distal end of a surgical instrument is that portion furthest away from the surgeon when in use, and the proximal end is that portion generally closest to the user.

It will be appreciated that embodiments of the disclosure described herein may be comprised of one or more conventional processors and unique stored program instructions that control the one or more processors to implement, in conjunction with certain non-processor circuits and other elements, some, most, or all of the functions of ultrasonic surgical instruments described herein. The non-processor circuits may include, but are not limited to, signal drivers, clock circuits, power source circuits, and user input and output elements. Alternatively, some or all functions could be implemented by a state machine that has no stored program instructions, in one or more application specific integrated circuits (ASICs), in which each function or some combinations of certain of the functions are implemented as custom logic, or in a field-programmable gate array (FPGA) enabling the use of updateable custom logic either by the manufacturer or the user. Of course, a combination of the three approaches could also be used. Thus, methods and means for these functions have been described herein.

From the foregoing, and with reference to the various figure drawings, those skilled in the art will appreciate that certain modifications may also be made to the present disclosure without departing from the scope of the same. While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. An electrosurgical generator comprising:
   a radio frequency (RF) amplifier having an inverter configured to convert a direct current (DC) to an alternating current (AC);
   a plurality of sensors configured to sense voltage and current of generated electrosurgical energy; and
   a controller coupled to the RF amplifier and the plurality of sensors;
   wherein the controller is configured to:
   generate a control signal for controlling the inverter;
   determine a power level based on sensed voltage and sensed current;
   determine a power efficiency of the inverter based on the determined power level; and drop a predetermined integer number of cycles from the control signal to form cycles having no pulse signals when the power efficiency of the inverter reaches a threshold power efficiency, the predetermined integer number of the cycles being dropped from the control signal at random times.

2. The electrosurgical generator according to claim 1, wherein a duty cycle is varied to facilitate maintenance of a desired power efficiency.

3. The electrosurgical generator according to claim 1, wherein an average power is maintained regardless of how many cycles of the control signal are dropped.

4. The electrosurgical generator according to claim 1, wherein the controller is further configured to switch from a continuous wave mode to a pulsed wave mode.

5. The electrosurgical generator according to claim 1, wherein a duty cycle is determined to maintain the determined power level at a desired power level.

6. The electrosurgical generator according to claim 5, wherein the duty cycle is varied to maintain a desired power efficiency.

7. The electrosurgical generator according to claim 1, wherein a pulse width is determined to maintain the determined power level at a desired power level.

8. The electrosurgical generator according to claim 7, wherein the pulse width is varied to maintain a desired power efficiency.

9. A method of improving efficiency of an electrosurgical generator, the method comprising:
   sensing voltage and current generated by an inverter of the electrosurgical generator;
   generating a control signal for controlling the inverter;
   determining a power level based on sensed voltage and sensed current;
   determining a power efficiency of the inverter of the electrosurgical generator based on the determined power level; and
   dropping a predetermined integer number of cycles from the control signal to form cycles having no pulse signals when the power efficiency of the inverter reaches a threshold power efficiency, the predetermined integer number of the cycles being dropped from the control signal at random times.

10. The method according to claim 9, further comprising varying a duty cycle to facilitate maintenance of a desired power efficiency.

11. The method according to claim 9, further comprising maintaining an average power regardless of how many cycles of the control signal are dropped.

12. The method according to claim 9, further comprising switching from a continuous wave mode to a pulsed wave mode.

13. The method according to claim 9, further comprising determining a duty cycle to maintain the determined power level at a desired power level.

14. The method according to claim 13, further comprising varying the duty cycle to maintain a desired power efficiency.

15. The method according to claim 9, further comprising determining a pulse width to maintain the determined power level at a desired power level.

16. The method according to claim 15, further comprising varying the pulse width to maintain a desired power efficiency.

* * * * *